United States Patent
Nakahana et al.

(10) Patent No.: US 8,228,498 B2
(45) Date of Patent: Jul. 24, 2012

(54) SAMPLE STORAGE

(76) Inventors: Yoko Nakahana, Hyogo (JP);
Shinichiro Kakuda, Hyogo (JP)

( * ) Notice: Subject to any disclaimer, the term of this patent is extended or adjusted under 35 U.S.C. 154(b) by 435 days.

(21) Appl. No.: 12/527,507

(22) PCT Filed: Mar. 9, 2009

(86) PCT No.: PCT/JP2009/054968
§ 371 (c)(1),
(2), (4) Date: Aug. 17, 2009

(87) PCT Pub. No.: WO2009/113694
PCT Pub. Date: Sep. 17, 2009

(65) Prior Publication Data
US 2011/0181875 A1 Jul. 28, 2011

(30) Foreign Application Priority Data

Mar. 13, 2008 (JP) .................................. 2008-064976
Jun. 10, 2008 (JP) .................................. 2008-152249

(51) Int. Cl.
*G01N 21/01* (2006.01)
(52) U.S. Cl. ..................................................... 356/244
(58) Field of Classification Search .................. None
See application file for complete search history.

(56) References Cited

U.S. PATENT DOCUMENTS 6,085,603 A    7/2000  Riekkinen
6,719,203 B2 *  4/2004  Hirono et al. ............ 235/462.13

FOREIGN PATENT DOCUMENTS

| EP | 1 210 979 A1 | 6/2002 |
| JP | 7-92170 | 4/1995 |
| JP | 3043865 | 12/1997 |
| JP | 11-174060 | 7/1999 |
| JP | 2001-502595 | 2/2001 |

* cited by examiner

*Primary Examiner* — Tu Nguyen
(74) *Attorney, Agent, or Firm* — Hamre, Schumann, Mueller & Larson, P.C.

(57) ABSTRACT

Sample storage, in which barcodes and two-dimensional codes printed on the outer surface of the sample storage can be read correctly. A storage tube 110 is transparent, comprising a top opening. An opaque writable outer element 120 covers storage tube 110 throughout from the bottom surface to the side surface. An opaque writable outer element 120 is a medium on which coded information that can be read by optical reading is written. The opaque writable outer element 120 is pushed in and irreversibly fixed to the storage tube 110 by a locking mechanism. At least one window 125 is provided, which enables a sample 200 contained to be observed, with the opaque writable outer element 120 installed outside. Accordingly, coded information written on the opaque writable outer element 120 can be read, and sample 200 observed through the window 125.

11 Claims, 12 Drawing Sheets

(a)

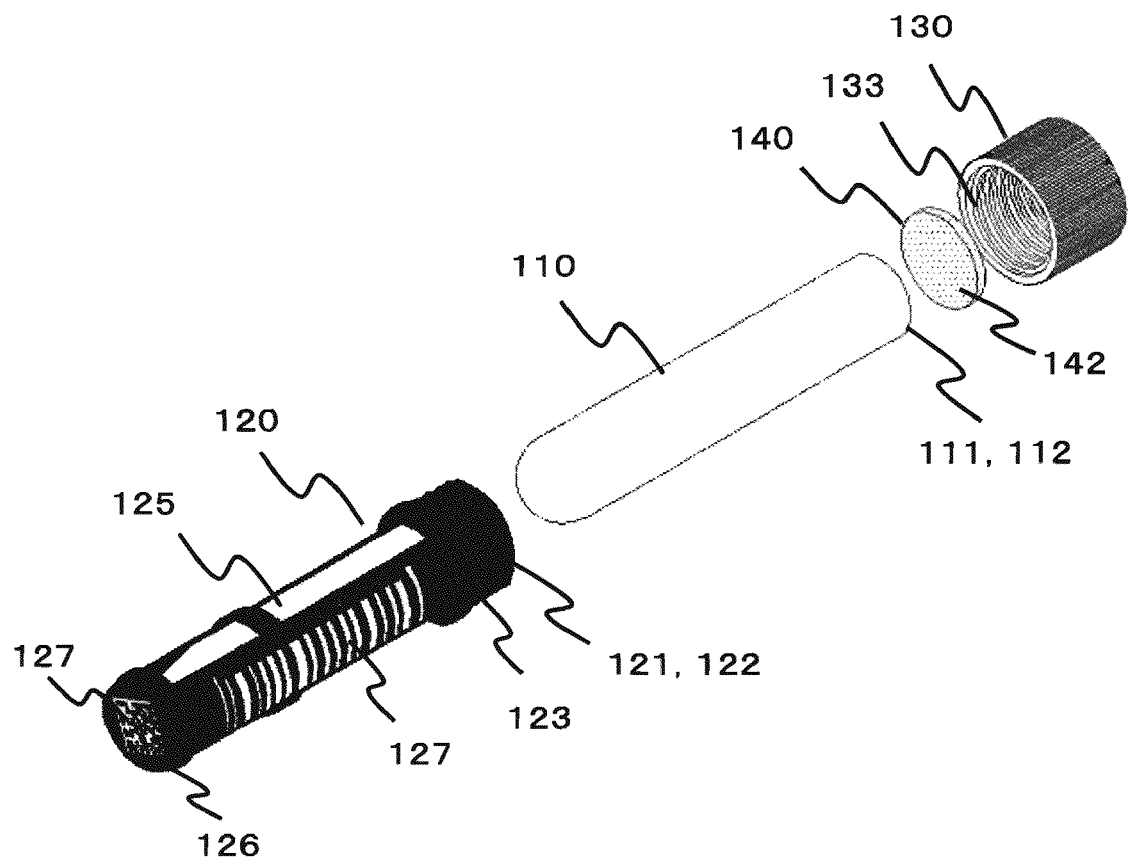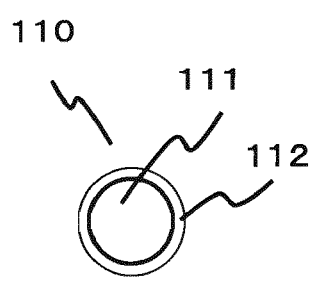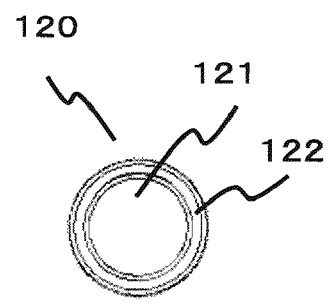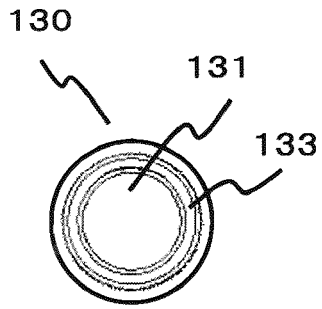
Fig. 3

Fig. 8   -- Prior Art --

(a) 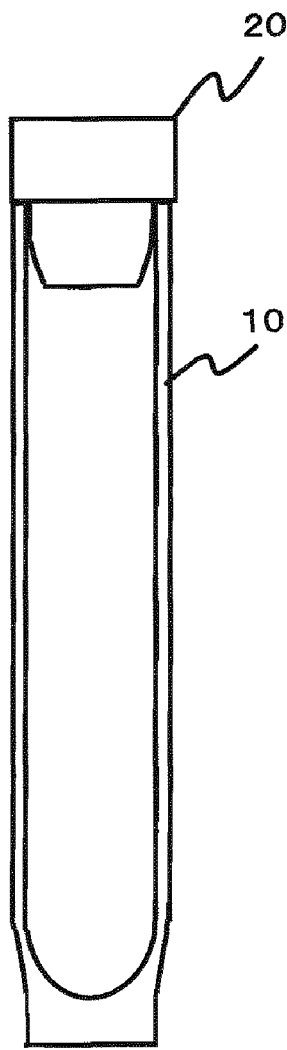 (b) 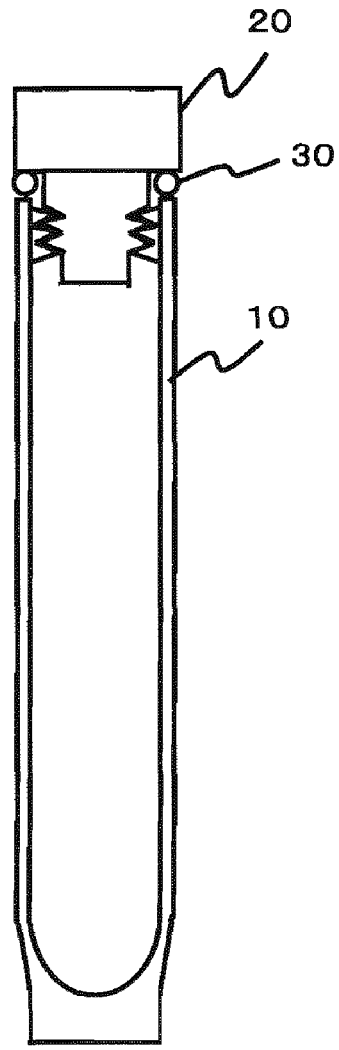
(Prior art)
Fig. 12

SAMPLE STORAGE

TECHNICAL FIELD

This invention relates to a sample storage that is used for storing a large number of samples, and applicable to various uses in storing samples. For example, it is used in enclosing and storing developing medicine samples. Also, it is used for storing samples that hold gene information of DNA in the medical field.

BACKGROUND ART

In the research and development of medicine and chemicals, storage tubes are used extensively in storing a large number of samples. For example, scientists prepare a large number of samples for a comparative experiment with slightly changing conditions such as blending amount, and they use storage tubes for storing the samples for a required period of time while handling them.

In order to control and store a large number of storage tubes at a time as described above, it is necessary to identify each storage tube. In the past they were identified by handwriting a sample name or identification number directly on the outer surface of storage tubes; however, in recent years sample storages that are controlled by printing a barcode or two-dimensional code on the side and/or bottom surface of the storage tube are highlighted, in which various data and/or control information of a sample are encoded. The barcode or two-dimensional code is read in a control process.

A sample storage of the prior art where a barcode or two-dimensional code is written on the side and/or bottom surface thereof is shown below. For example, a sample storage comprises a tubular container 10 that stores samples, and a lid element 20 that covers directly the top opening thereof as shown in FIG. 12 (a) or FIG. 12 (b).

Container 10 is a tube that stores samples, which forms a shape similar to a so-called test tube. Simple shaped storage tubes are used in many cases, since mounting a certain structure to container 10 may drive up costs. In this example, it is made of glass.

Lid element 20 is to cover the top opening of container 10, while for example lid element 20 shown in FIG. 12 (a) is a lid made of rubber or a plastic plug. The top opening of container 10 is plugged tightly, and then the top opening of container 10 is closed completely, by pushing lid element 20 into container 10.

Lid element 20 shown in FIG. 12 (b) is mounted to container 10 by screwing. The top opening of container 10 is plugged tightly, and the top opening of container 10 is closed completely, by turning and screwing lid element 20. A gasket 30 may be provided on the back of lid element 20.

DISCLOSURE OF THE INVENTION

The Problems to be Solved

The above sample storages of prior art can be controlled by writing a barcode or two-dimensional code directly on the side and/or bottom surface thereof using ink, etc., and then reading the barcode and/or two-dimensional code.

However, the above sample storages of prior art remain a matter to be improved as follows. There is a risk of false recognition due to superimposing of a barcode or two-dimensional code on the outer surface of the sample storage and a sample contained in the sample storage. The possibility of false recognition due to the superimposing on a sample contained in the sample storage may increase, especially when a bar code is present in a large form on the side surface. Since the typical use of sample storages is to handle the sample contained, container 10 is made of transparent material so that the condition of the sample contained can be checked visually. While black bars or dots are to be plotted on the surface of transparent container 10 when barcodes or two-dimensional codes are written directly on the outer surface of container 10, reading the barcodes or two-dimensional codes in such a condition may cause false recognition by the recognition systems, such as a scanner, because such black bars or dots plotted on the surface of container 10 are superimposed on the sample contained. Especially when the sample is not transparent liquid, and the color tone of the sample is deep or turbid, the possibility of false recognition by the recognition systems, such as a scanner, may increase. When humans visually check such codes, it may be difficult to read numbers and/or symbols.

Accordingly, both requirements that visual observation of the sample contained should not be obstructed, and that the color tone and turbidity of the sample contained should not affect the reading of barcodes or two-dimensional codes on the outer surface have to be satisfied together; however, conventional sample storages do not satisfy such two contradictive requirements.

In view of the above problem, the present invention aims at providing a sample storage that enables barcodes or two-dimensional codes on the outer surface of the sample storage to be read correctly without false recognition, which satisfies both requirements that visual observation of the sample contained should not be obstructed, and that the color tone and turbidity of the sample contained should not affect the reading of barcodes or two-dimensional codes on the outer surface.

Means of Solving the Problems

To achieve the above purpose, a sample storage according to the present invention, comprises; a storage tube having a top opening, which is made of light-transmissive material to enable a sample contained to be observed, an opaque writable outer element used as a medium to which coded information that can be read by optical reading has already been directly written, which is installed outside by covering said storage tube throughout from the bottom surface to the side surface, a locking mechanism to fix irreversibly upon pushing said storage tube into said opaque writable outer element, which is provided between the inner wall of said opaque writable outer element and the outer wall of said sample storage, and at least one window on said opaque writable outer element, provided in the area other than the write area where said coded information is written, which enables said sample contained to be observed;

which enables said coded information written to said opaque writable outer element to be read, and said sample contained to be observed through said window.

The above coded information write area includes such cases that the coded information is written to said coded information write areas that correspond to the bottom surface of said storage tube, to said coded information write area that corresponds to the side surface of the said storage tube, or to said coded information write area that corresponds both to the bottom surface and the side surface thereof.

With the sample storage according to the present invention, the above opaque writable outer element can be fixed to the above storage tube by the above locking mechanism without an adhesive agent.

In the above embodiment, it is preferable that the above opaque writable outer element is made of opaque plastic material to disable the above storage tube from being viewed through the above coded information write area, so that the color tone and turbidity of the above sample contained in the above storage tube do not affect the reading of the above coded information by the above optical reading.

In the above embodiment, the sample contained can be checked visually, and the color tone and turbidity of the sample may not affect the reading because barcodes or two-dimensional codes may not be superimposed on the sample contained, since the barcodes or two-dimensional codes are written to an opaque write medium.

It is preferable that the color of the opaque writable outer element is black, which is hardly affected regardless of the color tone and turbidity of the sample contained, and shields against light. Accordingly, the color of the opaque writable outer element should be black.

There are two different writing methods of coded information to opaque writable outer elements in relation to the color of barcodes or dot-codes and the material color of opaque writable outer elements.

The first writing method is to express the above coded information written directly on the above opaque writable outer element by changing the color of the area other than bars or dots of the above coded information to a different color from the above material color, while the material color of the above opaque writable outer element is the same as the color to be expressed as bars or dots of the above coded information.

The second writing method is to express the above coded information written directly to the above opaque writable outer element by changing the color of the area of bars or dots of the above coded information to a different color from the above material color, while the material color of the above opaque writable outer element is different from the color to be expressed as bars or dots of the above coded information.

In general barcodes and two-dimensional codes are expressed by contrast between two colors, and two colors of black and white have the highest contrast. While the color of part of the coded information write area is changed to white from black when the whole opaque writable outer element is black, the color of the area other than bars or dots is changed to white from black when the area of bars or dots is expressed black and the base is expressed white; on the contrary, the color of the area of bars or dots is changed to white from black when the area of bars or dots is expressed white and the base is expressed black.

A storage tube according to the present invention may be provided without any coded information written. In particular, the present invention provides a sample storage with an opaque writable outer element, comprising; a storage tube having a top opening, which is made of transparent or translucent light-transmissive material to enable the sample contained to be observed, an opaque writable outer element to be used as a medium to which coded information that can be read by optical reading will be written, which is installed outside by covering the above storage tube throughout from the bottom surface to the side surface, a locking mechanism to fix irreversibly upon pushing the above storage tube into the above opaque writable outer element, which is provided between the inner wall of the above opaque writable outer element and the outer wall of the above sample storage, and at least one window on the above opaque writable outer element, which is provided in the area other than the write area where the above coded information is written, which enables the above sample contained to be observed; which enables the above coded information to be written directly on the above opaque writable outer element, and the above sample contained to be observed through the above window.

Effect of the Invention

A sample storage according to the present invention enables barcodes or two-dimensional codes on the outer surface thereof to be written directly to an opaque writable outer element, and the barcodes or two-dimensional codes to be read correctly without false recognition because the opaque writable outer element is not imposed on a sample contained, since the barcodes or two-dimensional codes are written to an opaque write medium.

BRIEF DESCRIPTION OF THE DRAWINGS

FIG. 3(a)-(d) are exploded views of a sample storage 100, which explodes into individual components.

FIG. 12(a)-(b) are schematic views of a sample storage 10 of conventional art.

DETAILED DESCRIPTION OF THE PREFERRED EMBODIMENT

Some embodiments of a sample storage according to the present invention are described below in reference to the relevant drawing. Needless to add, the claims of the present invention include but are not limited to the application, configuration, or quantity shown in the following embodiments.

Embodiment 1

A sample storage 100 in embodiment 1 according to the present invention is described.

Figure 1:
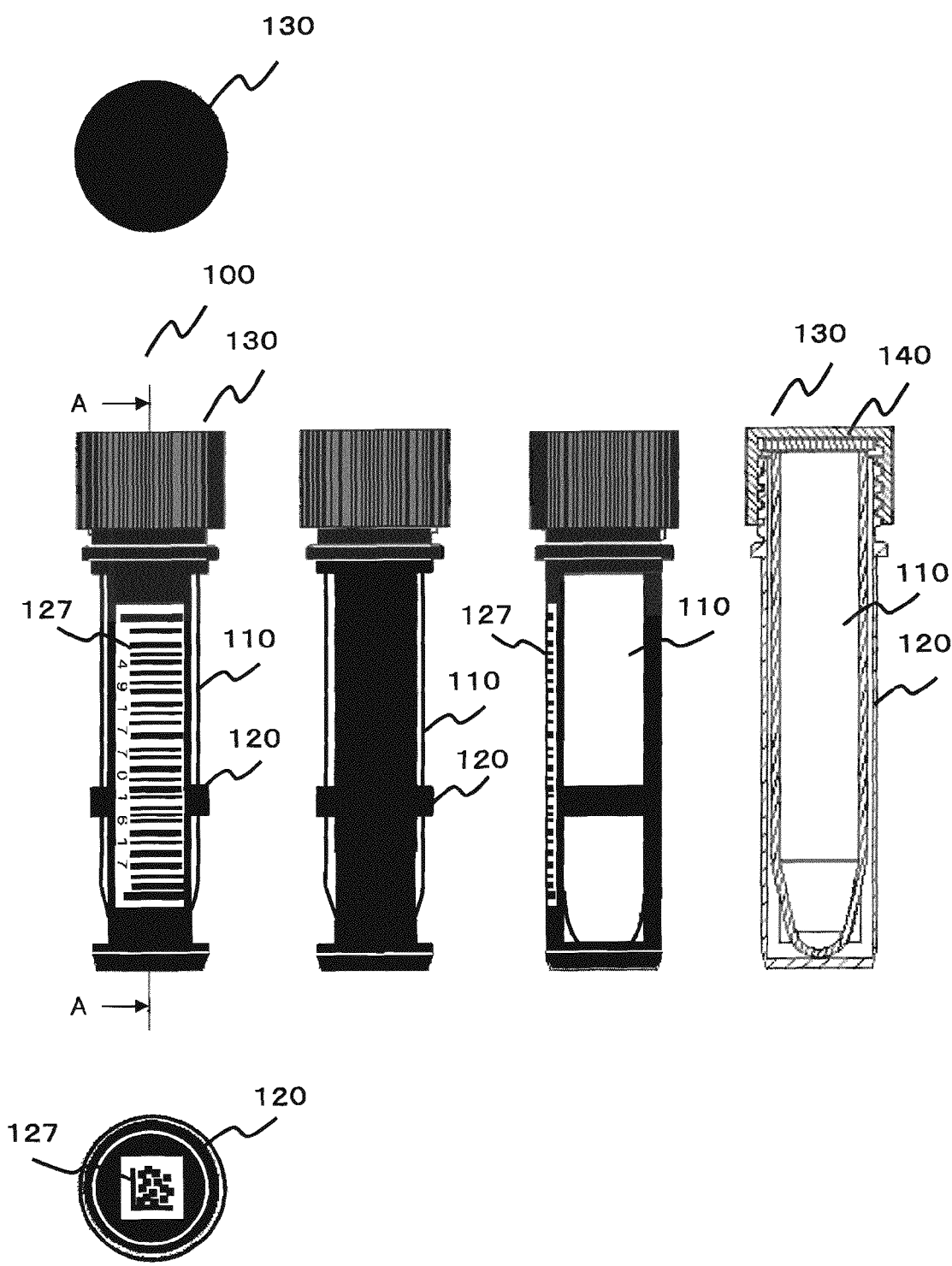
FIG. 1 is a schematic view of a sample storage 100 in embodiment 1.
Figure 2:
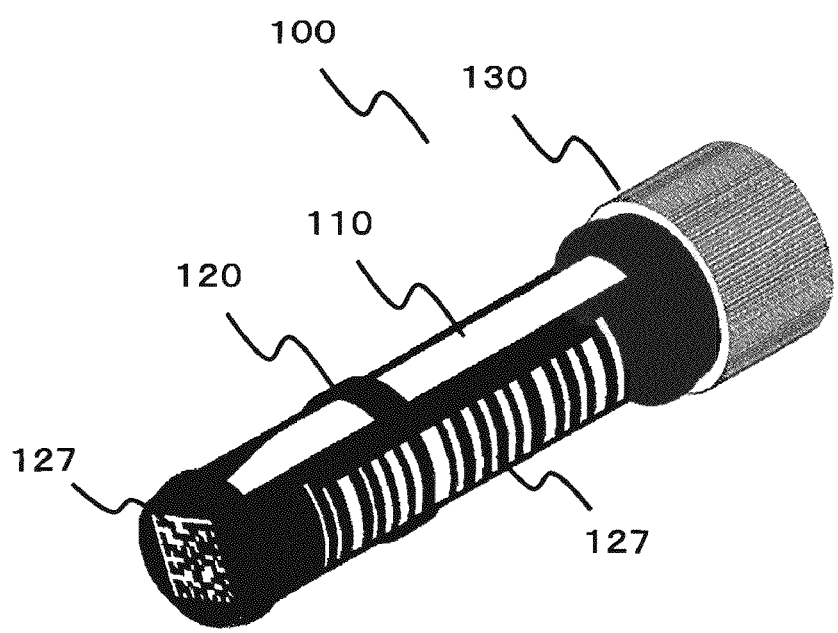
FIG. 2 is a perspective view of a sample storage 100 in embodiment 1.

FIG. 1 is a schematic view of a sample storage 100 in embodiment 1 according to the present invention. A front view, right side view, back view, top view, bottom view, and A-A cross-sectional view are shown. FIG. 2 is a perspective view, and FIG. 3 is an exploded view of a sample storage 100, which explodes into individual components.

As shown in FIG. 1 through FIG. 3, a sample storage 100 in embodiment 1 comprises a storage tube 110, an opaque writable outer element 120, a lid element 130, and a gasket 140.

While the material color of opaque writable outer element 120 is black as shown in FIG. 1, but in some other figures, the black coloring of the opaque writable outer element 120 is omitted for the purpose of better visualization and explanation of other aspects. In addition, the coded information 127, one-dimensional barcodes or two-dimensional dot codes, comprises black bars or black dots, but in some figures, just the outline of the bars or dots without black coloring is drawn for the purpose of better visualization and explanation of other aspects.

Storage tube 110 is a tubular container having a top opening 111 on the top surface, which stores samples. A top edge 112 of the top opening forms a flat surface, that faces a bottom surface 142 of gasket 140 as described hereinbelow. In this embodiment, storage tube 110 forms a tubular shape; however, it may form other forms according to its intended use, etc. Storage tube 110 is made of transparent or translucent light-transmissive material. Any material that is suitable for sample storages and that enables the sample contained to be observed is applicable, including plastic such as polypropylene, and glass. When translucent material is used in order to reduce the effect of ultraviolet rays, etc., any material that enables the sample contained to be observed is applicable, even if it is colored white or brown.

Opaque writable outer element 120 is installed outside to the storage tube 110 throughout from the bottom surface to the side surface, and is used as a medium in which coded information can be written directly, as is installed outside to storage tube 110. In this embodiment, its original color is black, but the original black color can be changed to white by method described hereinafter. In some figures, the black coloring is omitted for the purpose of better visualization and explanation.

The inner wall of opaque writable outer element 120 forms a tubular shape, so that the inner wall of opaque writable outer element 120 just fits to the outer shape of the storage tube 110. It is installed outside directly to the storage tube 110 by fitting without adhesive agent. Storage tube 110 and opaque writable outer element 120 are fixed irreversibly by a locking mechanism 160 as described hereinbelow.

The outer wall of opaque writable outer element 120 does not necessarily form such a test tube shape as storage tube 110, and it may form various shapes.

There is a top opening 121 on the top of the opaque writable outer element 120. The storage tube 110 is inserted to the opaque writable outer element 120 through the top opening 121. A top edge 122 of the opening of opaque writable outer element 120 forms a flat surface.

A thread 123 is formed on the outer wall on the top of the opaque writable outer element 120. In this embodiment, the thread 123 is a male screw. The thread 123 is screwed together with the thread 133 formed on the inner wall of lid element 130 as described hereinbelow. In another configuration, the thread 123 may be formed near the top of storage tube 110, but not on the opaque writable outer element 120. The thread 123 on the storage tube 110 may be a male screw, and the thread 133 on the lid element 130 may be a female screw; on the contrary, the thread 123 on the storage tube 110 may be a female screw, and the thread 133 on the lid element 133 may be a male screw, which is to be screwed in.

In this embodiment, the storage tube 110, the opaque writable outer element 120, and the lid element 130 are integrated by fixing irreversibly the storage tube 110 and the opaque writable outer element 120 by the lock mechanism 160, and by screwing the lid element 130 to the storage tube 110.

The side surface of the opaque writable outer element 120 forms a side surface writable area 124, which is used as a space to write coded information, such as barcodes and two-dimensional codes. While any area can be a writable area because the color of the opaque writable outer element 120 can be changed in color from black of the original base color to white as described below, a limited part of the side surface is used as a side surface writable area 124 in this embodiment. Thus, once identification information is given to the side surface writable area 124 on the side surface by printing barcodes or two-dimensional codes, the identification information of the sample storage 100 can be read by non-contact scanning of the side surface writable area 124 from the side of the sample storage 100.

A window 125 is formed in the area other than the side surface writable area 124 on the side surface of the opaque writable outer element 120, so that the storage tube 110 can be observed from the outside. Conditions of the stored sample easily can be observed from the outside through the window 125.

In this embodiment, a flat disc shaped bottom surface writable area 126 is formed at the bottom end of the opaque writable outer element 120. This bottom section acts to have the sample storage 100 stand by itself, and to form the bottom surface writable area 126, which is used as a medium to which the code such as the two-dimensional codes can be printed. As described above, the opaque writable outer element 120 is installed to the outside throughout from the bottom surface to the side surface, and the bottom surface writable area 126 forms an area that is used as a medium to which the code such as the two-dimensional codes are printed. Thus, once identification information is given to the bottom surface writable area 126 by printing the two-dimensional codes, the identification information of the sample storage 100 can be read by non-contact scanning of the bottom surface writable area 126 from the bottom of the sample storage 100.

Figure 4:
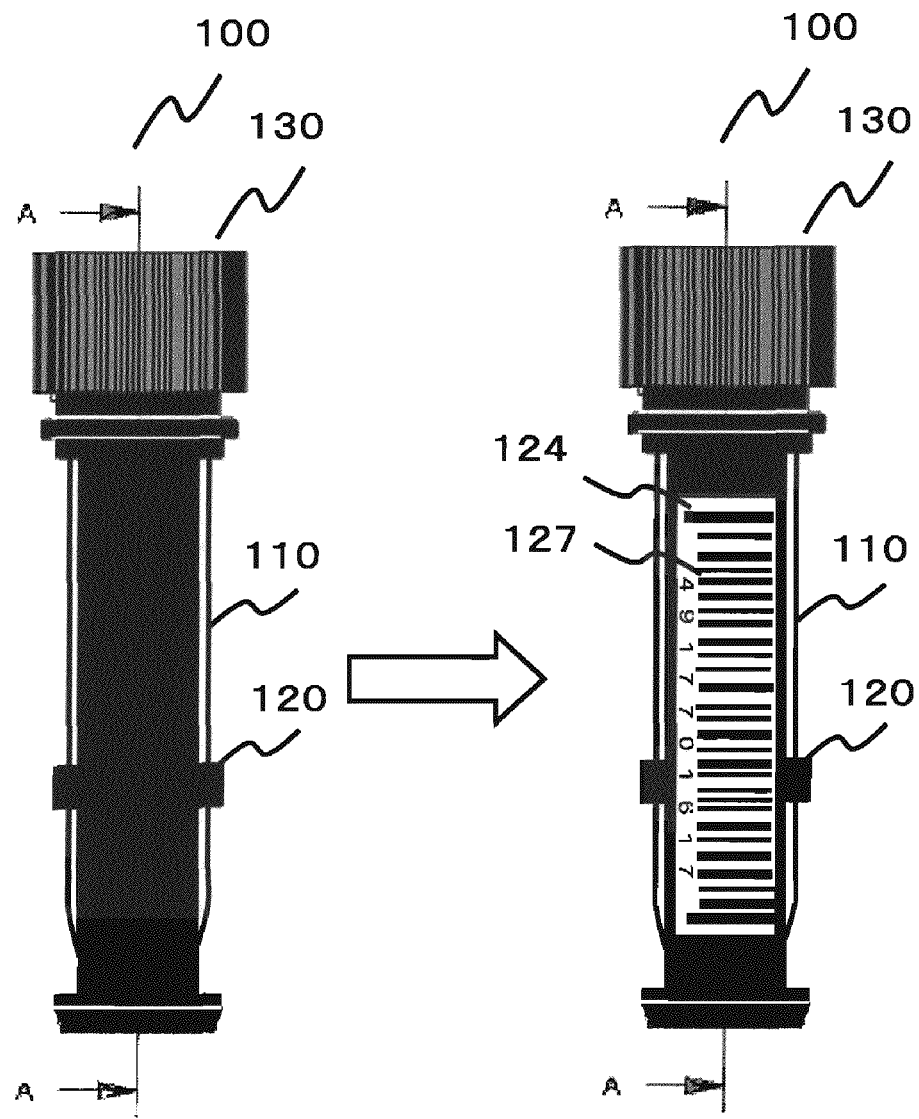
FIG. 4 is a schematic view of an embodiment showing how to write coded information to an opaque writable outer element 120.

FIG. 4 shows an embodiment of how to write coded information to the opaque writable outer element 120. FIG. 4 (a) shows the opaque writable outer element 120 before writing the coded information. Its color is original black base. It is a feature that the black base of the opaque writable outer element 120 is the same color as that of bars or dots that comprise barcodes or two-dimensional codes. The surface of the opaque writable outer element 120 is coated with the resin whose color is changed physically to white by heating in this embodiment.

FIG. 4 (b) shows that the color changing of the area other than bars or dots, which becomes the base area where the bar code or dot code is defined, is changed to white from black using a thermal head. In this embodiment, a barcode is formed. Thus, coded information can be written directly to the opaque writable outer element 120, by changing the color of the base area other than bars or dots portion, but not writing bars or dots with black ink.

In this embodiment, coded information is formed on both the side surface writable area 124 on the side surface, and the bottom surface writable area 126.

While the lid element 130 is to plug a top opening 111 of the storage tube 110, the top opening 121 on the top of the opaque writable outer element 120 is closed by the inner back side 131 of the lid element 130 in this embodiment.

In this embodiment, the thread 133 is formed on the inner wall surface of the lid element 130, which is screwed together with the thread 123 on the opaque writable outer element 120; however, other configurations are possible. For example, the thread 123 is formed on the storage tube 110, but not on the opaque writable outer element 120, the thread 133 on the lid element 130 is screwed together with the thread 123 on the storage tube 100. In addition, as described above, the thread 123 on the storage tube 110 may be a male screw, and thread 133 on lid element 130 may be a female screw; on the contrary, the thread 123 on the storage tube 110 may be a female screw, and the thread 133 on the lid element 130 may be a male screw, which is to be screwed in.

The lid element 130 and the opaque writable outer element 120 are fixed firmly when the thread 133 on the lid element 130 is screwed together with the thread 123 on the opaque writable outer element 120. The storage tube 110 that is inserted to the opaque writable outer element 120 is enclosed and blocked by the opaque writable outer element 120, the lid element 130, and the gasket 140.

The gasket 140 intervenes between the top of the storage tube 110 and the inner back side 131 of the lid element 130, which seals directly the top opening 111 of the storage tube 110.

Next, the locking mechanism 160 is described. The locking mechanism 160 is to fit and fix irreversibly the storage tube 110 to the opaque writable outer element 120. The fine detail figure of the locking mechanism 160 is omitted in FIG. 3, the outer wall of the storage tube 110 and the inner wall of the opaque writable outer element 120 are fixed irreversibly, having an appropriate mechanism that enables both to fit and fix to each other. Accordingly, they are not disconnected easily once they are irreversibly fixed to each other.

Figure 5:
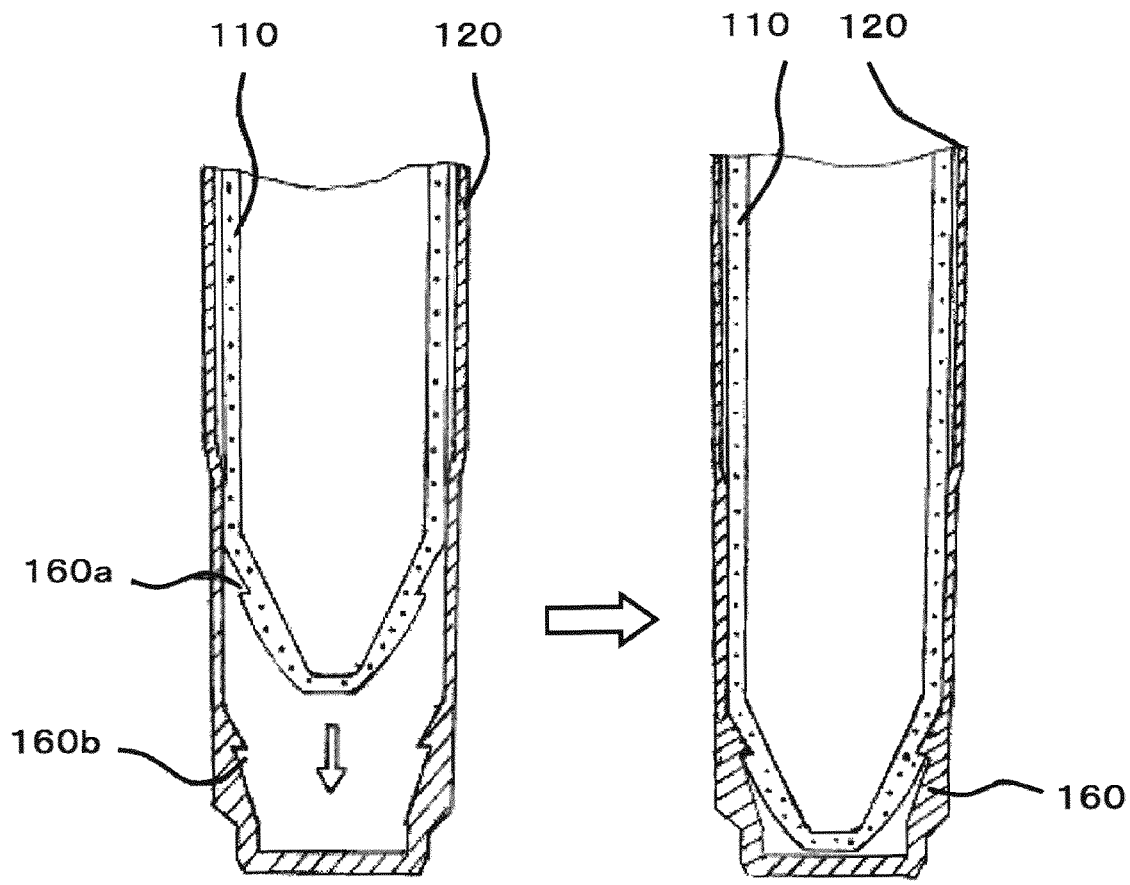
FIG. 5 is a sectional view of an embodiment of a locking mechanism 160 for sample storages of the type shown in FIG. 1 through FIG. 3.

There are various mechanisms of the locking mechanism 160, without particular limitation. An embodiment is shown in FIG. 5. FIG. 5 is a cross-sectional view of an embodiment of the locking mechanism 160 for sample storages of the type shown in FIG. 1 through FIG. 3. A locking mechanism 160a, comprising a projection having a "barb", is formed on the outer wall of the storage tube 110, and a locking mechanism 160b, a corresponding "slit", is formed on the inner wall of the opaque writable outer element 120. Once they are fitted to each other, they are fixed together and not disconnected easily.

FIG. 5 (left) shows the condition in the process of inserting the storage tube 110 to the opaque writable outer element 120, whereas FIG. 5 (right) shows the condition after the storage tube 110 has been inserted and irreversibly fixed to the opaque writable outer element 120. Here, "fixing irreversibly" means that the storage tube 110 and the opaque writable outer element 120 cannot be disconnected unless the respective male and female sections being fitted to each other are mechanically broken.

Figure 6:
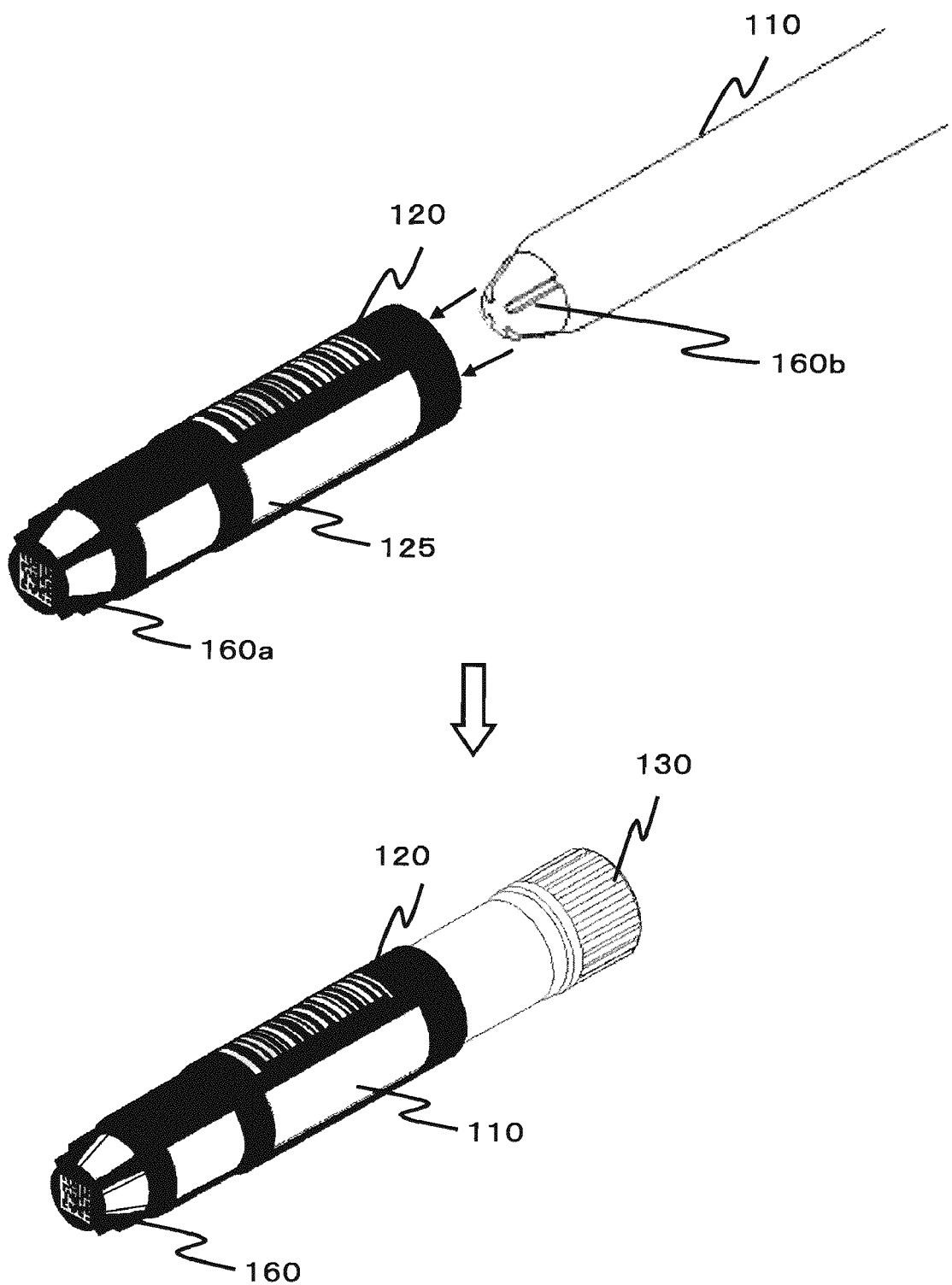
FIG. 6 is a perspective view of a locking mechanism 160 for a sample storage of the type not shown in FIG. 1 through FIG. 3.

FIG. 6 is a perspective view of a locking mechanism 160 for a sample storage of the type not shown in FIG. 1 through FIG. 3. A multiple bladed locking mechanism 160a, which acts as a "barb", is formed near the end on the inner wall of the opaque writable outer element 120. There is a locking mechanism 160b, comprising multiple "slits" corresponding to the blades on the outer wall of the storage tube 110; therefore, both are fixed and not disconnected easily once fixed to each other.

As described above, there are various mechanism of the locking mechanism 160, without particular limitation.

Sample storage 100 in embodiment 1 according to the present invention comprises such components as described above.

Carrying of information by the barcodes or two-dimensional codes written in the sample storage 100 according to the present invention is described below. Human visual checking of the sample contained in a sample storage 100 and recognition by the recognition system of barcodes and two-dimensional codes according to the present invention are described.

Figure 7:
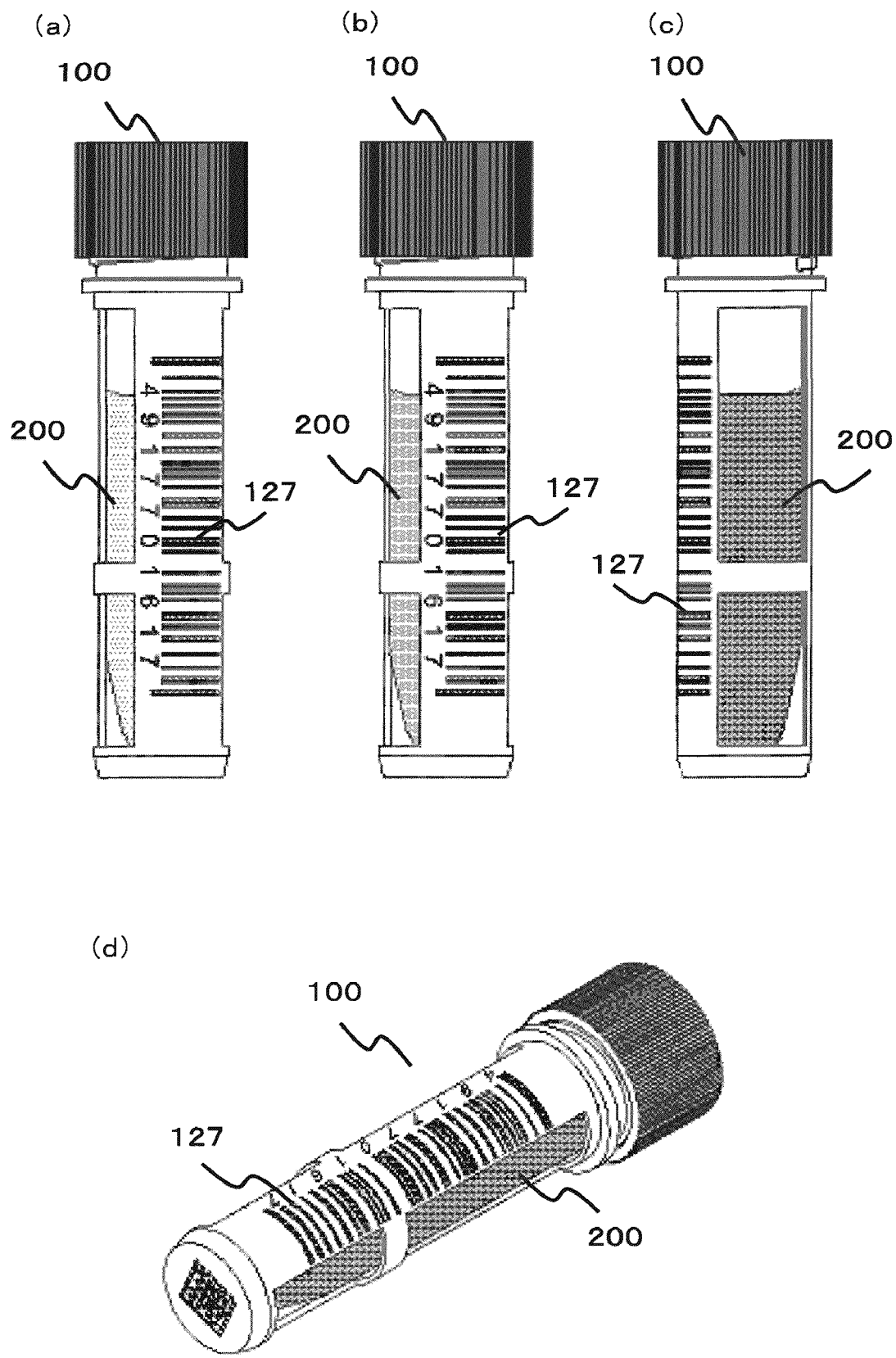
FIG. 7(a)-(d) show schematic views at various angles of a sample storage 100 with a sample contained.

FIG. 7 shows schematic views at various angles of the sample storage 100 with a sample 200 contained. The sample colors are lighter to deeper in order of FIG. 7 (a), FIG. 7 (b), and FIG. 7 (c).

The opaque writable outer element 120 is made of opaque (for example, black) plastic material, so the storage tube 110 is invisible through a side surface writable area 124. As a result, the color tone and turbidity of sample 200 contained in the storage tube 110 do not affect in reading coded information by means of optical reading, as shown in any of FIG. 7 (a), FIG. 7 (b), and FIG. 7 (c). Accordingly, barcodes on the side surface writable area 124 are viewed clearly. As shown in FIG. 7 (d), the storage tube 110 is invisible from the bottom through the bottom surface 126, and the color tone and turbidity of sample 200 contained in the storage tube 110 do not affect the reading of coded information by means of optical reading. Accordingly, barcodes on the bottom surface writable area 126 are viewed clearly.

Figure 8:
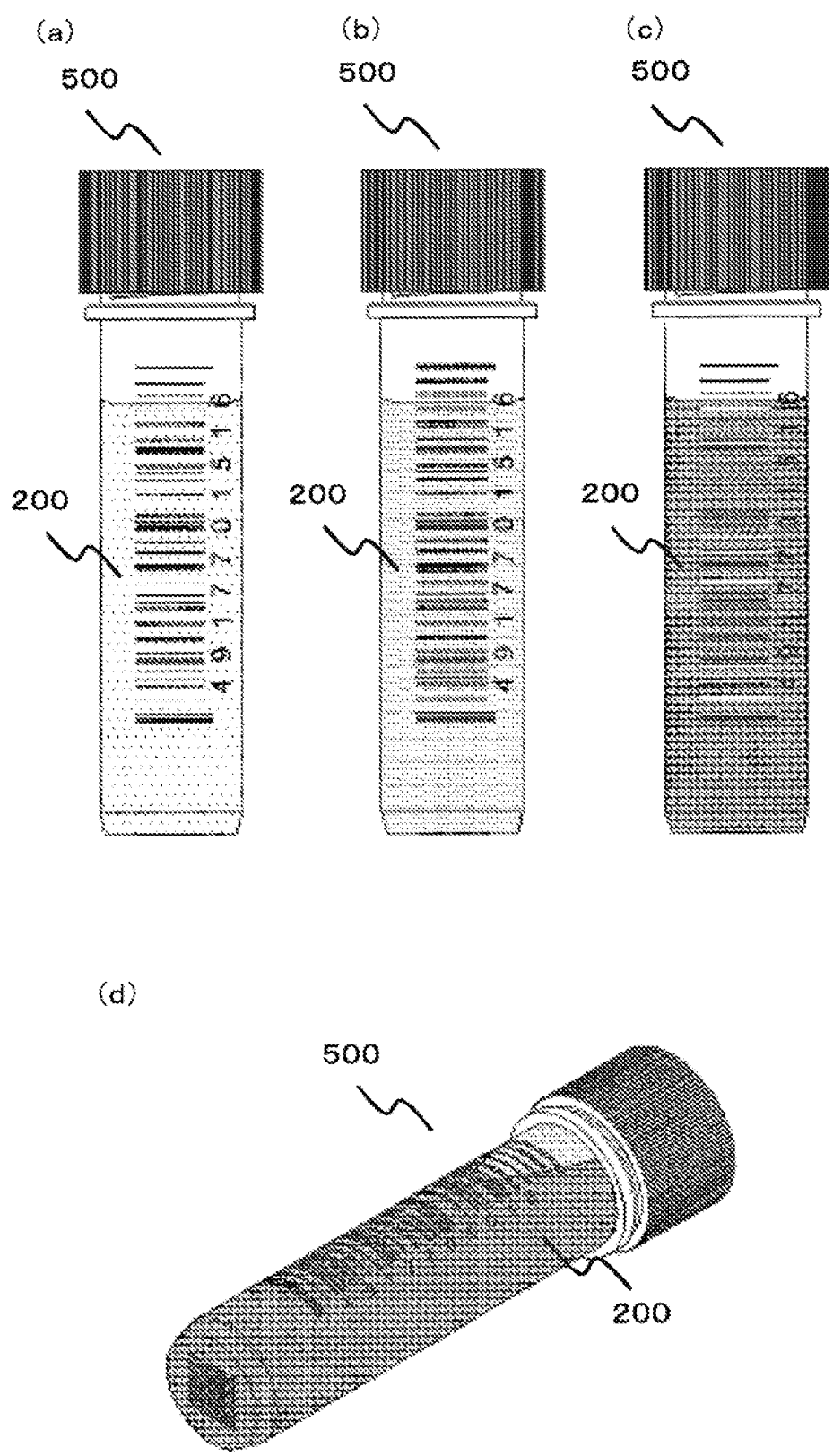
FIG. 8(a)-(d) show schematic views of a sample storage 500 of conventional art with a sample contained.

FIG. 8 shows schematic views of a conventional sample storage 500 with a sample 200 contained. The colors of the sample 200 are lighter to deeper in order of FIG. 8 (a), FIG. 8 (b), and FIG. 8 (c). As shown in any of FIG. 8 (a), FIG. 8 (b), and FIG. 8 (c), the color tone and turbidity of the sample 200 contained in the storage tube 500 may affect the reading of coded information by means of optical reading. The barcodes printed directly on the outer surface of such storage tubes are superimposed on the sample 200 when barcodes are printed directly, because the sample storage 500 of the conventional art is made of transparent or translucent light-transmissive material. As a result, the sample 200 contained can not be viewed clearly. Accordingly, barcodes on the side surface writable area 124 may not viewed clearly, which may cause false recognition. As shown in FIG. 8 (d), the color tone and turbidity of the sample 200 contained in the storage tube 500 may affect the reading of coded information by means of optical reading from the bottom. Accordingly, two-dimensional codes on the side surface writable area 126 may not be viewed clearly, which may cause false recognition.

As described above, barcodes or two-dimensional codes may not be superimposed on the sample 200, the color tone and turbidity of the sample 200 may not affect the reading of them, so the sample can be visually checked through the window 125, and barcodes and two-dimensional codes are written to the opaque media (the side surface writable area 124, and the bottom surface writable area 126). Accordingly, barcodes and two-dimensional codes may not be superimposed on the sample 200 contained, and the color tone and turbidity of the sample 200 may not affect the reading of them.

Various control methods using the above sample storage 100 can be assumed depending on its use without particular limitation. For example, every data item related to the sample storage 100 is checked and controlled by a computer using an allotted index, each measured value is checked with the predetermined high and low limits, and when the data is out of the range, a retry of measurement, a report of detection of errors, or a warning is performed. In the above checking processing, the average of multiple measured values can be used instead of each measured value. When some data is contaminated or damaged under storage or test, the sample storage of the present invention can provided several functions such as the function for detecting a wrong lid insertion and replacing right lid by comparison check of the lid elements with the opaque writable outer elements, the function for a human error backup function for amending and recovering based on multiple data matching by reading the same data from lid area and side area. In addition, sample storage 100 may be stored in a sample storage rack, controlled and stored by a computer, automatically picked out when it is used in a test, and then transferred to a specified position to use the sample to the test. Also, the operations to plug a lid element and store to the storage position may be automatically operated by a computer after the test is completed.

Embodiment 2

Figure 9:
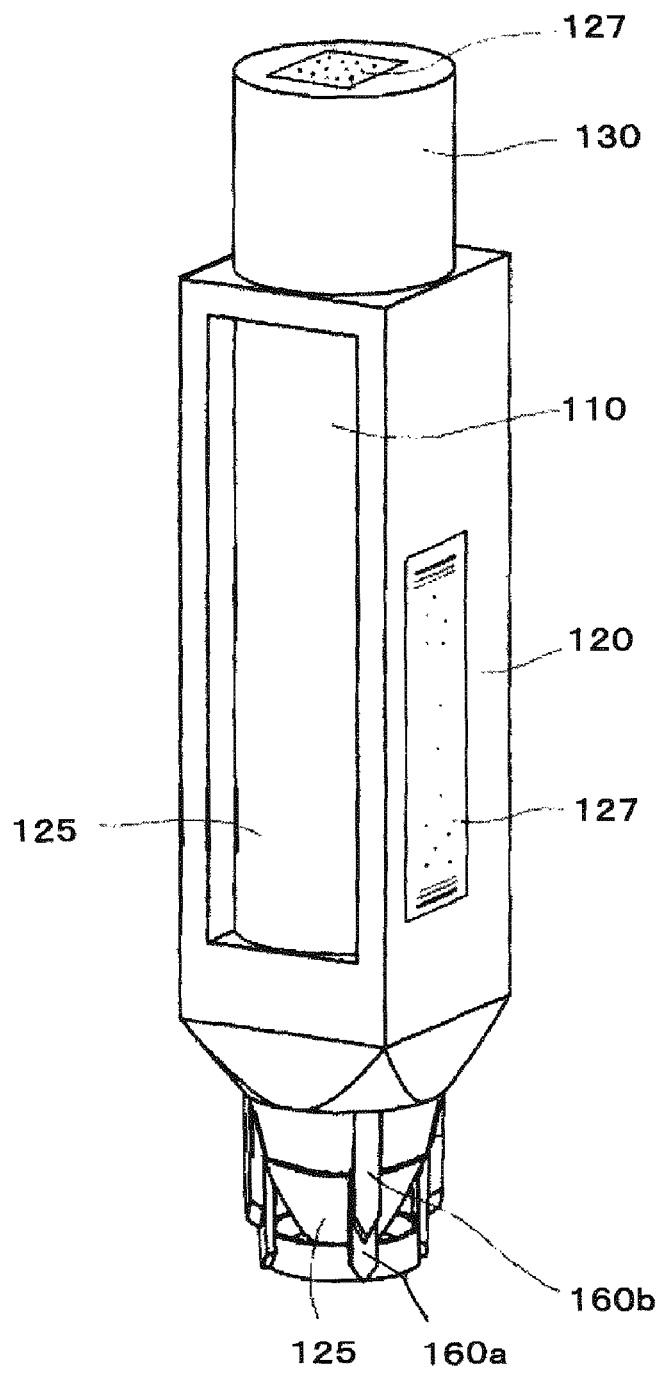
FIG. 9 is a perspective view of a sample storage 100a in embodiment 2.

FIG. 9 is a perspective view of the sample storage 100a in embodiment 2. In this embodiment, a blade is formed at four corners on the bottom of the opaque writable outer element 120, and a female shaped locking mechanism 160b is formed inside the base of each blade. The opaque writable outer element 120 comprises a white polypropylene molded part that forms a square tubular shape, having a large opening 125.

While the storage tube 110 forms a tubular shape with a cup-shaped bottom, a male shaped locking mechanism 160a with a so-called "barb" is provided annularly outside the bottom.

A lid element 130 comprises an opaque white polyethylene molded part. Samples can be sealed properly according to the property of the sample stored in the storage tube 110, for example, by using melamine resin or other materials having equivalent hardness, such as phenol resin, for lid element 130, and by intervening a silicon or fluorine-based resin gasket between the top flat surface of the sample storage 110 and the lid element 130.

When the storage tube 110 is pushed into the opaque writable outer element 120, both are fixed irreversibly in such a way that the male shaped locking mechanism 160a provided outside the bottom of the storage tube 110 is fitted to the female shaped locking mechanism 160b provided inside the blade on the bottom of the opaque writable outer element 120.

Thus, once the storage tube 110 is pushed into the opaque writable outer element 120, both are fixed irreversibly by locking mechanism 160b.

Embodiment 3

Figure 10:
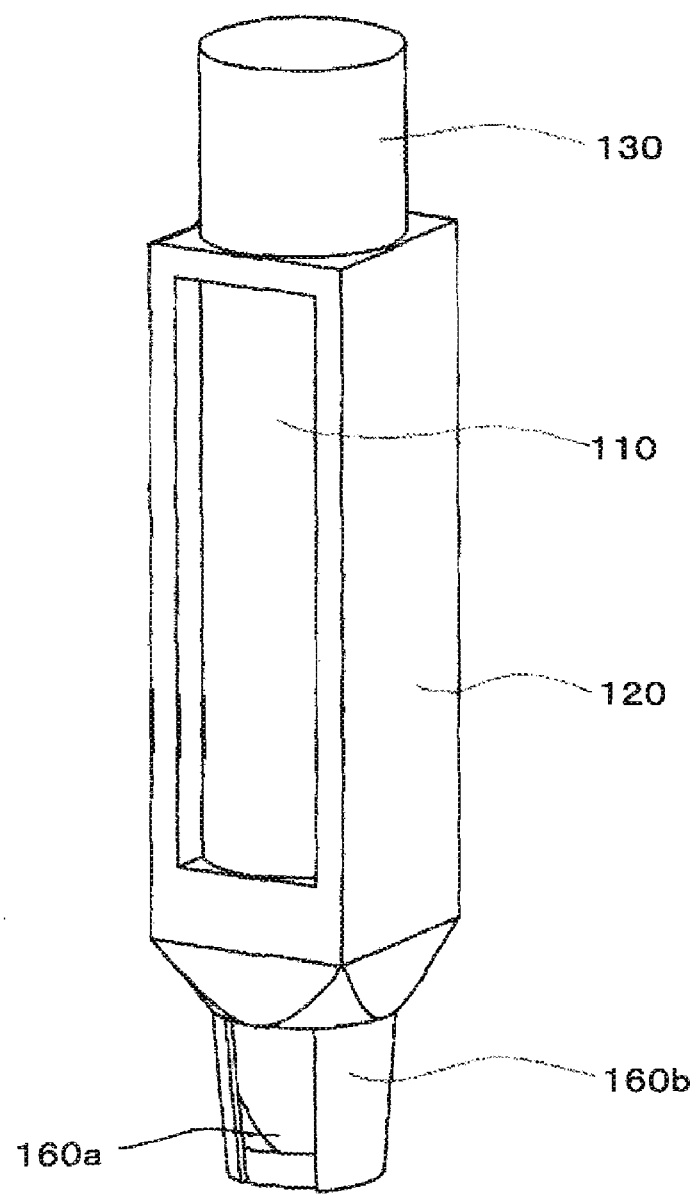
FIG. 10 is a perspective view of a sample storage 100b in embodiment 3.

FIG. 10 is a perspective view of a sample storage 100b in embodiment 3. The storage tube 110, a transparent hard glass Sptizy-type sample storage, forms a tubular shape with a cup-shaped bottom.

The opaque writable outer element 120 comprises a white polypropylene molded part that forms a square tubular shape bottom. The locking mechanism 160 forms is defined by the mechanism as described hereinbelow.

The lid element 130 may be the same element as shown in embodiment 2.

Figure 11:
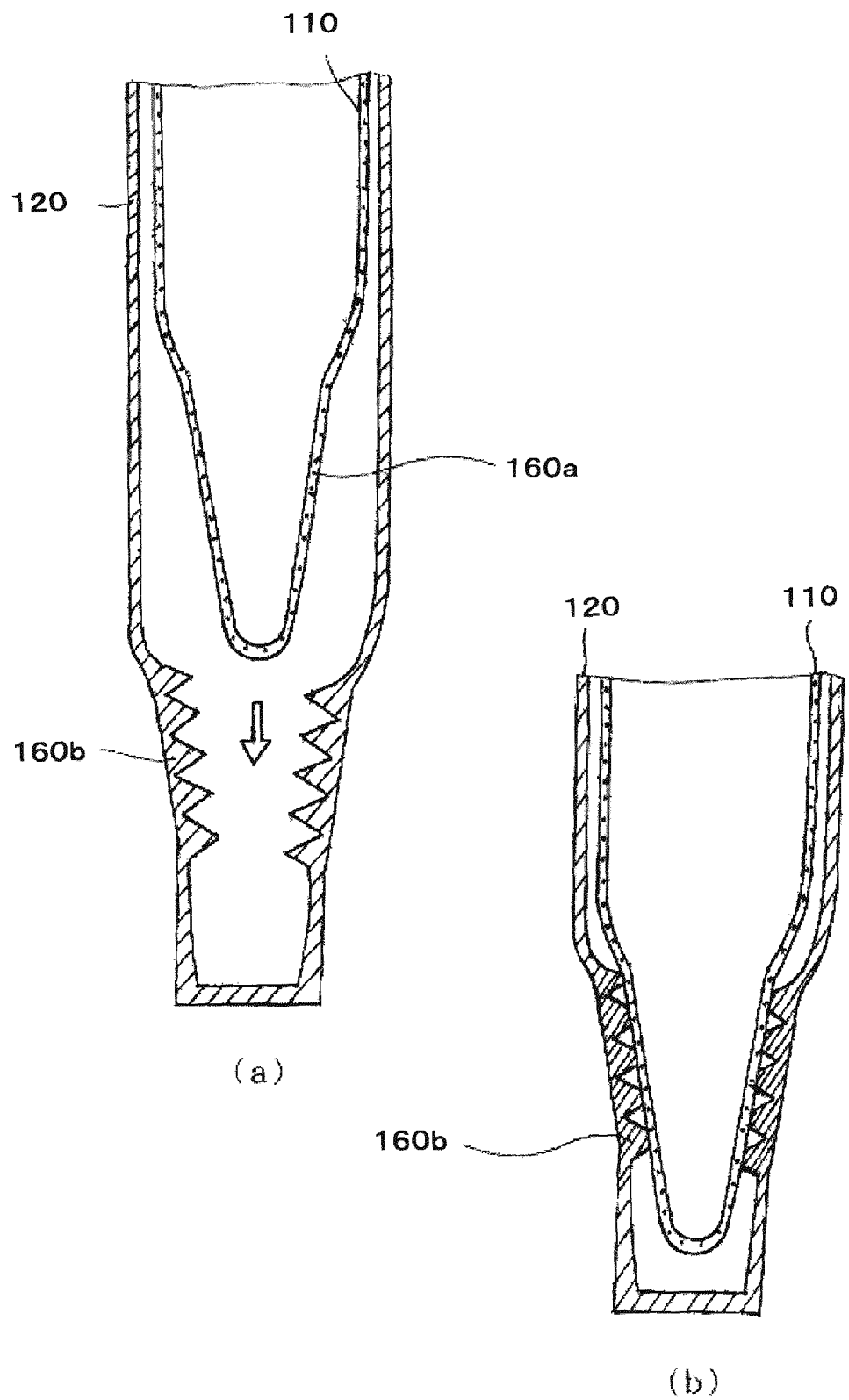
FIG. 11(a)-(b) are schematic views of a locking mechanism that fixes a storage tube 110 to an opaque writable outer element 120 in embodiment 3.

FIG. 11 is a schematic view of the locking mechanism 160 that fixes the storage tube 110 to the opaque writable outer element 120 in embodiment 3. In this embodiment, the locking mechanism 160b is provided on the inner wall of the opaque writable outer element 120, which forms a tubular shape being slightly reduced toward the bottom. Spiral grooves similar to the inner surface of nuts, having a large number of parallel concavo-convex shapes, are provided on the inner wall other than window area.

FIG. 11 (a) is a sectional view around the bottom end of the storage tube 110. In this embodiment, a hard glass Spitzy type storage tube forms a truncated cone shape, comprising a locking mechanism 160a having an outside diameter slightly larger than the inside diameter of the locking mechanism 160b on the opaque writable outer element 120.

FIG. 11 (b) is a sectional view of the storage tube 110, which is inserted to the opaque writable outer element 120 by applying pressure. When the storage tube 110 is inserted, it is fixed to the opaque writable outer element 120, while the locking mechanism 160b that has grooves similar to a thread of nuts, which is provided on the inner wall of the opaque writable outer element 120, deforms elastically and develops friction with the locking mechanism 160a on the bottom end of the storage tube 110.

Thus, once the storage tube 110 is pushed into the opaque writable outer element 120, both are fixed irreversibly by locking mechanism 160.

While some preferable embodiments of the sample storage according to the present invention are described above, it should be understood that various changes are possible, without deviating from the technical scope according to the present invention. Therefore, the technical scope according to the present invention is limited only by the claims attached.

INDUSTRIAL APPLICABILITY

A sample storage according to the present invention can be used extensively for storing a large number of samples. For example, it can be used as a sample storage for enclosing and storing drug samples. Also, it can be used as a sample storage for storing such samples that hold gene information of DNA in the medical field.

The invention claimed is:

1. A sample storage, comprising;
    a storage tube having a top opening, which is made of light-transmissive material to enable a sample contained to be observed,
    an opaque writable outer element used as a medium to which coded information that can be read by means of optical reading has already been directly written, which is installed to the outside by covering said storage tube throughout from the bottom surface to the side surface,
    a locking mechanism to fix irreversibly upon pushing said storage tube into said opaque writable outer element, which is provided between the inner wall of said opaque writable outer element and the outer wall of said sample storage,
    and at least one window on said opaque writable outer element, provided in the area other than the write area where said coded information is written, which enables said sample contained to be observed;
    which enables said coded information written to said opaque writable outer element to be read, and said sample contained to be observed through said window.

2. A sample storage comprising an opaque writable outer element as claimed in claim 1, in which said coded information is written to coded information write areas that correspond both to the bottom surface and the side surfaces of said storage tube.

3. A sample storage comprising said opaque writable outer element as claimed in claim 1, in which said opaque writable outer element is made of opaque plastic material to disable said storage tube from being viewed through said coded information write area, so that the color tone and turbidity of said sample contained in said storage tube do not affect reading of said coded information by said optical reading.

4. A sample storage comprising the opaque writable outer element as claimed in claim 1, in which said opaque writable outer element can be fixed to said storage tube by said locking mechanism without adhesive agent.

5. A sample storage as claimed in claim 1, in which the material color of said opaque writable outer element is the same as the color to be expressed as bars or dots of said coded information, and said coded information directly written to said opaque writable outer element is expressed by changing the color of the area other than bars or dots of said coded information to a different color from said material color.

6. A sample storage as claimed in claim 1, in which the material color of said opaque writable outer element is different from the color to be expressed as bars or dots of said coded information, and said coded information directly written to said opaque writable outer element is expressed by changing the color of the area of bars or dots of said coded information to a different color from said material color.

7. A sample storage, comprising;
a storage tube having a top opening, which is made of light-transmissive material to enable a sample contained to be observed,
an opaque writable outer element to be used as a medium to which coded information that can be read by means of optical reading will be written, which is installed to the outside of said storage tube by covering throughout from the bottom surface to the side surface,
a locking mechanism to fix irreversibly upon pushing said storage tube into said opaque writable outer element, which is provided between the inner wall of said opaque writable outer element and the outer wall of said sample storage, and
at least one window on said opaque writable outer element, provided in the area other than the write area where said coded information is written, which enables said sample contained to be observed;
which enables said coded information to be written directly to said opaque writable outer element, and said sample contained to be observed through said window.

8. A sample storage comprising said opaque writable outer element as claimed in claim 7, in which said opaque writable outer element is made of opaque plastic material to disable said storage tube from being viewed through said coded information write area, so that the color tone and turbidity of said sample contained in said storage tube do not affect reading of said coded information by said optical reading.

9. A sample storage comprising the opaque writable outer element as claimed in claim 7, in which said opaque writable outer element can be fixed to said storage tube by said locking mechanism without adhesive agent.

10. A sample storage as claimed in claim 7, in which the material color of said opaque writable outer element is the same as the color to be expressed as bars or dots of said coded information, and said coded information directly written to said opaque writable outer element is expressed by changing the color of the area other than bars or dots of said coded information to a different color from said material color.

11. A sample storage as claimed in claim 7, in which the material color of said opaque writable outer element is different from the color to be expressed as bars or dots of said coded information, and said coded information directly written to said opaque writable outer element is expressed by changing the color of the area of bars or dots of said coded information to a different color from said material color.

* * * * *